United States Patent
Anai et al.

(10) Patent No.: US 9,226,812 B2
(45) Date of Patent: Jan. 5, 2016

(54) BILIARY STENT

(71) Applicants: KAWASUMI LABORATORIES, INC., Saiki-shi, Oita (JP); PUBLIC UNIVERSITY CORPORATION NARA MEDICAL UNIVERSITY, Kashihara-shi, Nara (JP)

(72) Inventors: Hiroshi Anai, Kashihara (JP); Toshiyasu Yuba, Tokyo (JP)

(73) Assignees: KAWASUMI LABORATORIES, INC., Saiki-shi (JP); PUBLIC UNIVERSITY CORPORATION NARA MEDICAL UNIVERSITY, Kashihara-shi (JP)

( * ) Notice: Subject to any disclaimer, the term of this patent is extended or adjusted under 35 U.S.C. 154(b) by 0 days.

(21) Appl. No.: 14/373,173

(22) PCT Filed: Jan. 28, 2013

(86) PCT No.: PCT/JP2013/051796
§ 371 (c)(1),
(2) Date: Jul. 18, 2014

(87) PCT Pub. No.: WO2013/115141
PCT Pub. Date: Aug. 8, 2013

(65) Prior Publication Data
US 2014/0379092 A1  Dec. 25, 2014

(30) Foreign Application Priority Data

Jan. 30, 2012 (JP) .................................. 2012-016681

(51) Int. Cl.
*A61F 2/04* (2013.01)
*A61F 2/915* (2013.01)
(Continued)

(52) U.S. Cl.
CPC . *A61F 2/04* (2013.01); *A61F 2/915* (2013.01); *A61F 2/07* (2013.01); *A61F 2/24* (2013.01); *A61F 2002/041* (2013.01); *A61F 2002/91575* (2013.01); *A61F 2230/0008* (2013.01)

(58) Field of Classification Search
CPC ............... A61F 2/82; A61F 2/90; A61F 2/91; A61F 2/95
USPC ........................................ 623/1.15–1.35, 23.7
See application file for complete search history.

(56) References Cited

U.S. PATENT DOCUMENTS 6,200,335 B1 * 3/2001 Igaki ............................ 623/1.15
6,746,489 B2 * 6/2004 Dua et al. ................... 623/23.68
(Continued)

FOREIGN PATENT DOCUMENTS

JP     7-275369 A    10/1995
JP  2003-525691 A     9/2003
(Continued)

OTHER PUBLICATIONS

International Search Report for PCT/JP2013/051796 dated Apr. 16, 2103 [PCT/ISA/210].
(Continued)

*Primary Examiner* — Suzette J Gherbi
(74) *Attorney, Agent, or Firm* — Sughrue Mion, PLLC

(57) ABSTRACT

The purpose of the present invention is to provide a biliary stent making it possible to sufficiently exhibit a valve function while reducing the entire length of the biliary stent as compared to conventional ones. The present invention is a biliary stent (1) including a stent body (10), a tubular membrane (30) on one end of the stent body (10) and having a bile outflow port (34), and two support members (40, 50) which at one end (42, 52) are connected to the one end of the stent body (10) and at the other end (44, 54) are connected to the vicinity of the bile outflow port (34).

15 Claims, 8 Drawing Sheets

(51) Int. Cl.
  *A61F 2/07*  (2013.01)
  *A61F 2/24*  (2006.01)

(56) References Cited

U.S. PATENT DOCUMENTS

| | | | |
|---|---|---|---|
| 7,025,791 B2* | 4/2006 | Levine et al. | 623/23.64 |
| 7,118,600 B2* | 10/2006 | Dua et al. | 623/23.68 |
| 8,002,825 B2* | 8/2011 | Letac et al. | 623/2.14 |
| 8,282,678 B2* | 10/2012 | Yachia et al. | 623/1.13 |
| 2001/0041929 A1* | 11/2001 | Oepen | 623/1.15 |
| 2005/0021124 A1* | 1/2005 | Cunniffe et al. | 623/1.11 |
| 2005/0065614 A1* | 3/2005 | Stinson | 623/23.68 |
| 2006/0079955 A1* | 4/2006 | Brown | 623/1.22 |
| 2006/0149351 A1* | 7/2006 | Smirthwaite et al. | 623/1.13 |
| 2006/0229695 A1* | 10/2006 | Brown et al. | 623/1.3 |
| 2012/0310327 A1* | 12/2012 | McHugo | 623/1.15 |
| 2014/0025158 A1* | 1/2014 | Liddy et al. | 623/1.15 |
| 2014/0155981 A1* | 6/2014 | Ferrera et al. | 623/1.12 |
| 2015/0045876 A1* | 2/2015 | Clerc et al. | 623/1.38 |

FOREIGN PATENT DOCUMENTS

| | | |
|---|---|---|
| JP | 2003-531674 A | 10/2003 |
| JP | 2005-504602 A | 2/2005 |
| WO | 00/41652 A1 | 7/2000 |
| WO | 01/28459 A1 | 4/2001 |
| WO | 2004/047686 A1 | 6/2004 |
| WO | 2006/083763 A1 | 8/2006 |

OTHER PUBLICATIONS

Written Opinion for PCT/JP2013/051796 dated Apr. 16, 2103 [PCT/ISA/237].

Notification of Transmittal of International Search Report and Written Opinion for PCT/JP2013/051796 dated Apr. 16, 2103 [PCT/ISA/220].

Extended European Search Report, dated Oct. 21, 2015, issued in counterpart European Patent Application No. 13743741.4.

* cited by examiner

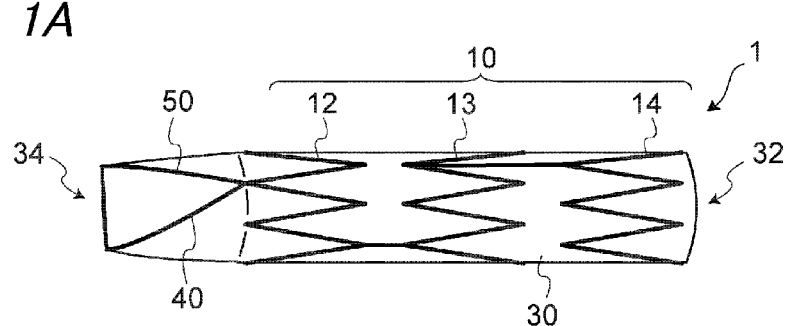
FIG. 1A
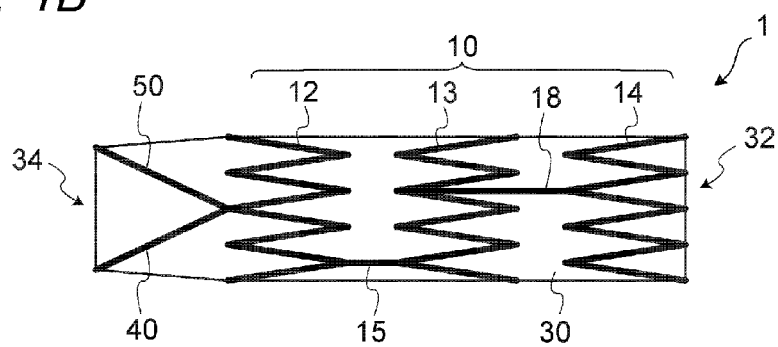
FIG. 1B
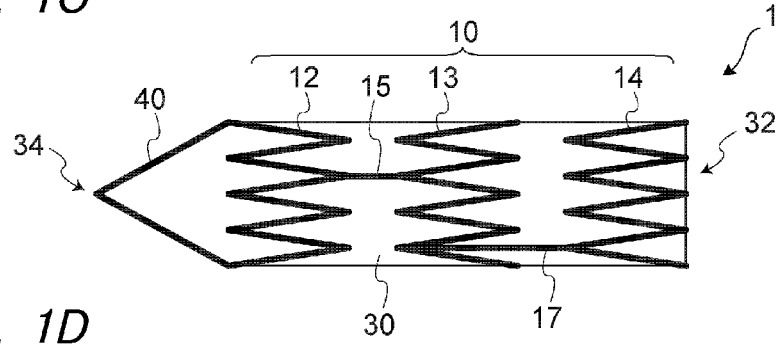
FIG. 1C
FIG. 1D
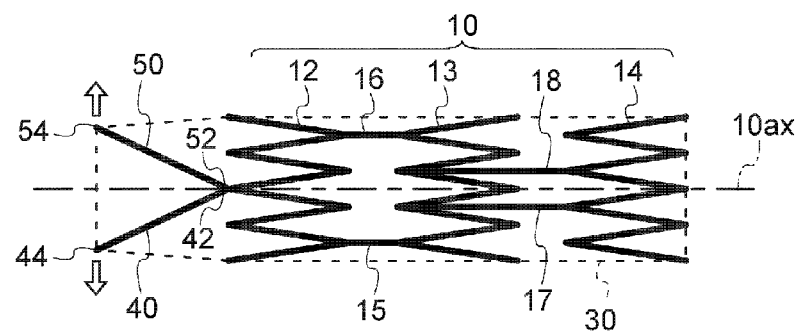

even if the entire length of the biliary stent is more shortened than conventional ones by reducing a length of the membrane, the valve function described above can be sufficiently exhibited.
BILIARY STENT

TECHNICAL FIELD

The present invention relates to a biliary stent.

BACKGROUND ART

As a surgical treatment for treating stricture or occlusion of a biliary tract, a 'biliary stent placement' is known, in which a radially expandable biliary stent is indwelled in a lesioned part. By performing the biliary stent placement, patency of the lesioned part in the biliary tract can be ensured and as a result, for example, remediation of obstructive jaundice symptoms can be achieved.

As biliary stents used for such a biliary stent placement, conventionally discussed biliary stents have a tubular stent body configured to be expandable and a membrane extending to protrude from one end of the stent body in a cylindrical manner (see, e.g., Patent Document 1). Conventional biliary stents are configured such that the membrane extends out toward a duodenum when being indwelled in a lesioned part of a biliary tract. The membrane is configured to allow bile flowed out from a gallbladder to be flowed toward the duodenum and also to prevent a backflow from the duodenum to the gallbladder. In this specification, a function of allowing bile flowed out from a gallbladder to flow toward the duodenum and also preventing a backflow from the duodenum to the gallbladder is referred as to 'valve function'.

PRIOR ART DOCUMENT

Patent Document

Patent Document 1: JP 7-275369 A

SUMMARY OF INVENTION

Problem to be Solved by Invention

However, at the site where such biliary stents are actually indwelled into bodies of patients, there is a desire to reduce the entire length of biliary stent as much as possible.

To address this desire, the entire length of biliary stent can be shortened as compared to with conventional biliary stents, if a length of the membrane of a conventional biliary stent is reduced. However, when the length of the membrane is simply reduced, it is considered to cause the following problems.

Specifically, if the length of the membrane is simply reduced in conventional biliary stents, there is a possibility that the membrane, which has been extended toward the duodenum, is turned over toward the gallbladder if a pressure exerted on the membrane from the duodenum side become higher as compared to a pressure exerted on the membrane from the gallbladder side. The membrane turned over toward the gallbladder cannot prevent a backflow from the duodenum to the gallbladder, and thus not exhibit a desired valve function.

The present invention has been made in view of the above problems, and an object thereof is to provide a biliary stent having sufficient valve function while reducing the entire length of the biliary stent as compared with conventional ones.

Means for Solving the Problem

A biliary stent (1) according to the present invention includes a tubular stent body (10) configured to be radially expandable, a tubular membrane (30) provided to protrude from one end of the stent body (10) and having a bile outflow port (34); and two support members (40, 50) supporting the membrane (30), wherein one end (42, 52) of each of the two support members (40, 50) is connected to the one end of the stent body (10), another end (44, 54) of each of the two support members (40, 50) is connected to a vicinity of the bile outflow port (34), and the two support members (40, 50) are arranged at locations opposed to each other and interposing a tube axis (10ax) of the stent body, and are configured to exert forces on the bile outflow port (34) along directions away from each other.

According to the biliary stent of the present invention, because two support members are arranged at locations opposed to each other and interposing the tube axis of the stent body, and are configured to exert forces on the bile outflow port along directions away from each other, the bile outflow port is closed in a linear shape (a substantially straight line) when no flow is present from a gallbladder toward a duodenum. If the biliary stent of the invention is indwelled in a biliary tract so that the membrane (the bile outflow port) is oriented toward the duodenum, bile from the gallbladder flows through the inside of the stent body and also the inside of the membrane, then from the bile outflow port toward the duodenum, whereas a backflow thereof from the duodenum to the gallbladder is prevented by the bile outflow port closed in a linear shape. Namely, a valve function can be exhibited by the membrane and two support members.

In addition, according to the biliary stent of the present invention, because each of the other ends of two support members is connected to the vicinity of the bile outflow port, even if a pressure exerted on the membrane from the duodenum side become higher as compared to a pressure exerted on the membrane from the gallbladder side, the membrane is not turned over toward the gallbladder, and thus a protruding direction of the membrane can be kept. As a result, the valve function described above can be sufficiently exhibited. Namely, even if the entire length of the biliary stent is more shortened than conventional ones by reducing a length of the membrane, the valve function described above can be sufficiently exhibited.

Accordingly, the biliary stent of the present invention has sufficient valve function while reducing the entire length of the biliary stent as compared with conventional ones.

According to the biliary stent (1) of the present invention, the biliary stent (1) is preferably configured to satisfy a relation of 2 L≥C, wherein L is a straight-line distance between the other ends (44, 54) of the two support members (40, 50) from which the membrane (30) is detached, and C is a peripheral length of the bile outflow port (34) of the membrane (30) from which the two support members (40, 50) are detached.

Although the details will be described below, by providing a configuration described above, the configuration that 'two support members exert forces on the bile outflow port along directions away from each other' can be achieved relatively easily.

According to the biliary stent (1) of the present invention, a shape of an end face of the bile outflow port (34) of the membrane (30) from which the two support members (40, 50) are detached is preferably flattened.

Considering that the bile outflow port is closed in a linear shape (a substantially straight line), it can be said that the closer the shape of the end face of the bile outflow port of the membrane is to the linear shape, the smaller the force required to close the bile outflow port will be. In addition, if the force required to close the bile outflow port is larger, there is a need to use materials having a relatively strong elastic force as materials for two support members and membrane, and materials to be used for two support members and membrane could be limited. According to the biliary stent of the present invention, because the shape of the end face the bile outflow port of the membrane is flattened and thus is of a shape relatively close to the linear shape, the force required to close the bile outflow port can be limited to be relatively small, and as a result, a flexibility in selection of materials for two support materials and membrane can be increased.

According to the biliary stent (1) of the present invention, preferably, the shape of the end face of the bile outflow port (34) is an ellipse, and the major radius of the ellipse is equal to or greater than two times the minor radius.

When the shape of the end face of the bile outflow port of the membrane is the ellipse having the major radius that is equal to or greater than two times the minor radius thereof, the shape is not so largely deviated from a shape of the bile outflow port when being closed. Therefore, for similar reasons described above, a biliary stent allowing a large flexibility in selection of materials for the two support members and the membrane can be achieved relatively easily.

According to the biliary stent (1) of the present invention, preferably, the shape of the end face of the bile outflow port (34) is configured such that a central portion with respect to a longitudinal direction of the end face is narrower than respective end portions.

When the shape of the end face of the bile outflow port of the membrane is configured such that the central portion in the longitudinal direction of the end face is narrower than the respective end portions, the bile outflow port can be firmly closed by forces exerted by two support members along directions away from each other.

According to the biliary stent (1) of the present invention, the two support members (40, 50) are preferably provided outside the membrane (30).

By configuring in this way, because two support members do not exist inside the membrane, generation of an undesired gap when the bile outflow port has been closed can be prevented.

According to the biliary stent of the present invention, the two support members are preferably provided inside the membrane.

By configuring in this way, the membrane can be relatively easily attached to cover two support members from the outside thereof upon fabrication, thereby promoting an easy fabrication of the biliary stent.

According to the biliary stent of the present invention, the two support members are preferably embedded in the membrane.

By configuring in this way, because two support members do not exist inside the membrane, generation of an undesired gap when the bile outflow port has been closed can be prevented. In addition, when the support members are made of a metal material, such a metal portion is not exposed, thereby reducing a risk of causing application of the biliary stent to be impossible due to a metal allergy.

According to the biliary stent (2) of the present invention, a tubular streamer portion (60) connected to the bile outflow port (34) is preferably additionally provided.

By configuring in this way, a backflow from the duodenum to the gallbladder can be further prevented and thus the valve function can be further enhanced.

The Reference signs in the parentheses next to the terms for each member or the like described in the claims and this section (the section of Means for Solving the Problem) are used to facilitate the understanding of the contents described in the claims and this section by referring to the drawings, and is not intended to limit the technical features described in the claims and this section.

Effects of Invention

According to the biliary stent of the present invention, when the biliary stent is indwelled in a biliary tract such that the membrane is oriented toward the duodenum, a valve function is provided by the membrane and the two support members. In addition, because each of the other ends of two support members is connected to the vicinity of the bile outflow port, the valve function described above can be sufficiently exhibited even if the entire length of the biliary stent is reduced as compared with conventional ones by reducing a length of the membrane.

BRIEF DESCRIPTION OF DRAWINGS

FIGS. 1A to 1D are views illustrating a biliary stent 1 according to a first embodiment, in which FIG. 1A is a perspective view schematically showing the biliary stent 1, FIG. 1B is a top view of the biliary stent 1, FIG. 1C is a side view of the biliary stent 1, and FIG. 1D is a view illustrating the biliary stent 1 and support members 40, 50.

FIGS. 2A to 2C are views illustrating a bile outflow port 34 in the biliary stent 1, in which FIG. 2A is an end view of the bile outflow port 34 when an internal pressure is not being exerted on the biliary stent 1, FIG. 2B is an end view of the bile outflow port 34 when an internal pressure is being exerted on the biliary stent 1, and FIG. 2C is an enlarged end view of the bile outflow port 34 shown in FIG. 2B.

FIGS. 3A to 3C are views illustrating a membrane 30, in which FIG. 3A is a perspective view of the membrane 30, FIG. 3B is an end view of the bile outflow port 34 of the membrane 30, and FIG. 3C is an end view of a bile outflow port 34 of a membrane 30 according to a variant of the first embodiment.

FIGS. 4A and 4B are views illustrating the support members 40, 50, in which FIG. 4A is a view showing the support members 40, 50 when the membrane 30 has been attached thereto, viewed from an upper surface direction thereof, and FIG. 4B is a view showing the support members 40, 50 when the membrane 30 has been detached therefrom, viewed from the upper surface side.

FIGS. 6A to 6E are views illustrating a biliary stent 2 according to a second embodiment, in which FIG. 6A is a perspective view schematically showing the biliary stent 2, FIG. 6B is a top view of the biliary stent 2, FIG. 6C is a side view of the biliary stent 2, FIG. 6D is an end view of a streamer portion 60 when a bile outflow port 34 is closed, and FIG. 6E is an end view of the streamer portion 60 when the bile outflow port 34 is opened.

FIGS. 7A and 7B are views illustrating a biliary stent 3 according to a third embodiment, in which FIG. 7A is a perspective view schematically showing the biliary stent 3 and FIG. 7B is a top view of the biliary stent 3.

FIGS. 9A and 9B are views illustrating a mock biliary tract 950 used in Test 1, in which FIG. 9A is a view showing the mock biliary tract 950 before each of samples is disposed therein and FIG. 9B is a view schematically showing a state where a fluid is communicated through a sample T indwelled in the mock biliary tract 950.

FIGS. 10A and 10B are views illustrating a mock biliary tract 970 used in Test 2, in which FIG. 10A is a view showing the mock biliary tract 970 before each of samples is disposed therein and FIG. 10B is a view schematically showing a state where a fluid is not communicated through a sample T indwelled in the mock biliary tract 970.

DESCRIPTION OF EMBODIMENTS

Figure 2A:
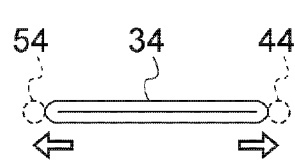

A biliary stent according to the present invention will be now described on the basis of embodiments shown in the drawings.

First Embodiment

First, configurations of a biliary stent 1 according to a first embodiment will be described with reference to FIGS. 1 to 3.

FIGS. 1A to 1D are views illustrating a biliary stent 1 according to the first embodiment. FIG. 1A is a perspective view schematically showing the biliary stent 1, FIG. 1B is a top view of the biliary stent 1, FIG. 1C is a side view of the biliary stent 1, and FIG. 1D is a view illustrating the biliary stent 1 and support members 40, 50. In FIG. 1D, a membrane 30 is shown by a broken line for easy understanding of the invention.

Figure 2B:
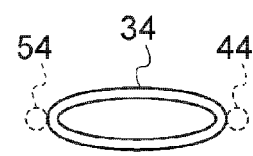
Figure 2C:
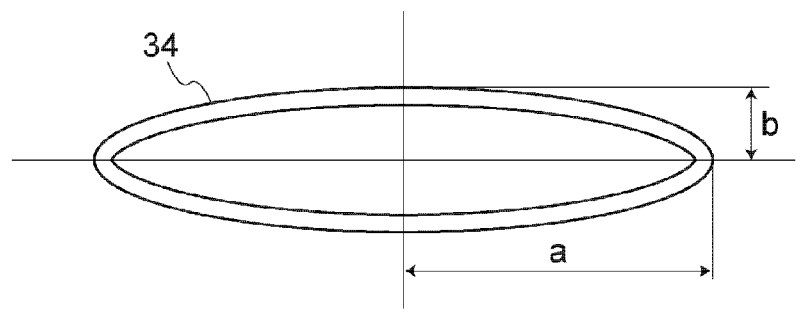

FIGS. 2A to 2C are views illustrating a bile outflow port 34 in the biliary stent 1. FIG. 2A is an end view of the bile outflow port 34 when an internal pressure is not being exerted on the biliary stent 1, FIG. 2B is an end view of the bile outflow port 34 when an internal pressure is being exerted on the biliary stent 1, and FIG. 2C is an enlarged end view of the bile outflow port 34 shown in FIG. 2B. In FIGS. 2A to 2C, a thickness of the membrane 30 and a size of each of the other ends 44, 54 of the support members 40, 50 in the bile outflow port 34 are shown in an exaggerated manner for easy understanding of the invention.

Figure 3A:
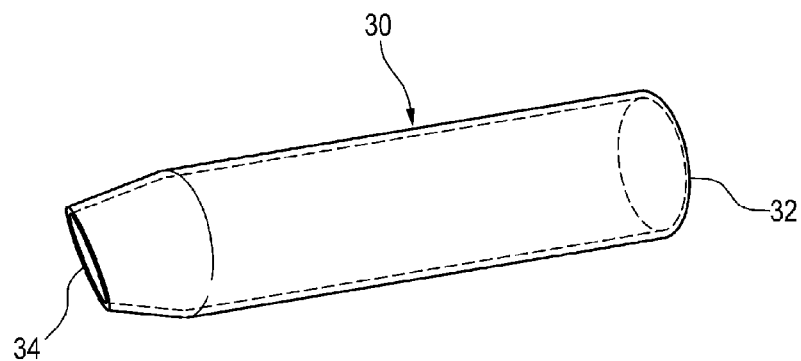
Figure 3B:
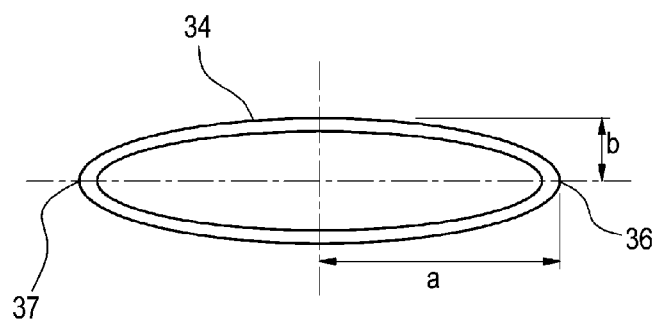
Figure 3C:
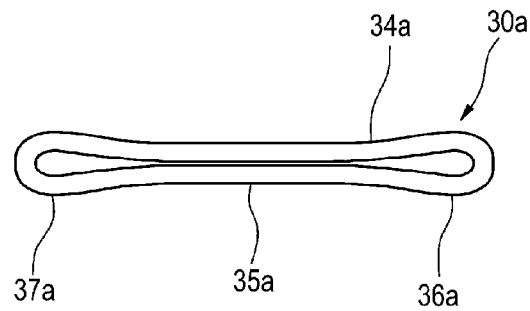

FIGS. 3A to 3C are views illustrating the membrane 30. FIG. 3A is a perspective view of the membrane 30, FIG. 3B is an end view of the bile outflow port 34 of the membrane 30, and FIG. 3C is an end view of a bile outflow port 34a of a membrane 30a according to a variant of the first embodiment. In FIGS. 3A and 3C, end surfaces of the bile outflow ports 34, 34a of the membranes 30, 30a from which two support members 40, 50 are detached are shown.

Figure 4A:
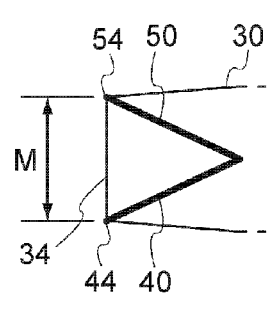
Figure 4B:
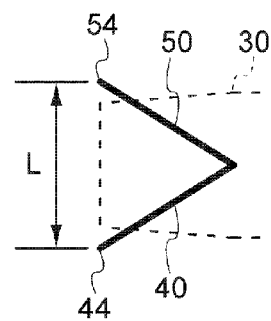

FIGS. 4A and 4B are views illustrating the support members 40, 50. FIG. 4A is a view showing the support members 40, 50 when the membrane 30 has been attached thereto, viewed from an upper surface direction thereof (the same direction as that in FIG. 1B), and FIG. 4B is a view showing the support members 40, 50 when the membrane 30 has been detached therefrom, viewed from the upper surface side.

As used herein, the term 'inside (or inward) of the stent body' means a region, which as viewing the stent body 10 (frames 12 to 14 described below) from a direction along a tube axis 10ax of the stent body, extends from wall surfaces of the frames 12 to 14 toward the tube axis 10ax of the stent body. Additionally, the term 'outside (or outward) of the stent body, means a region, which as viewing the stent body 10 (frames 12 to 14 described below) from a direction along the tube axis 10ax of the stent body, extends from wall surfaces of the frames 12 to 14 away from the tube axis 10ax of the stent body.

As shown in FIGS. 1A to 1D, the biliary stent 1 according to the first embodiment includes a tubular stent body 10 configured to be radially expandable, a tubular membrane 30 disposed inside the stent body 10, and two support members 40, 50 for supporting the membrane 30. The biliary stent 1 is, for example, a self-expandable biliary stent.

The stent body 10 has three frames 12, 13 and 14 arranged side by side and four connection members 15, 16, 17 and 18 for connecting the frames 12 to 14 to each other.

The frames 12 to 14 are formed by folding back a thin metal wire in a zigzag shape and are configured to have a cylindrical shape. The connection members 15 to 18 are similarly made, for example, of a thin metal wire, and are connected and fixed to a part of each of the frames 12 to 14. Preferably, a known metal or metal alloy typified, for example, by stainless steels, such as SUS316L, Ni—Ti alloys, Cu—Zn alloys, Ni—Al alloys, titanium alloys, or the like can be used as materials for the metal wires forming the frames 12 to 14 and the connection members 15 to 18.

The membrane 30 is provided to protrude from one end of the stent body 10 (an end on the frame 12 side) while covering an inner peripheral surface of the stent body 10. As shown in FIGS. 1A to 1C and 3A, the membrane 30 is of a tubular shape and has a bile inflow port 32 located on the frame 14 side thereof and a bile outflow port 34 located on the frame 12 side thereof.

The bile outflow port 34 can be constricted to allow two opposing sides thereof to be approached to each other. A shape of an end face of the bile outflow port 34 of the membrane 30 (a shape of an end face of the bile outflow port 34 of the membrane 30 when two support members 40, 50 has been detached therefrom) is an ellipse as shown in FIG. 3B. This ellipse is designed such that the major radius a is equal to or greater than two times the minor radius b thereof (a≧2b). In the first embodiment, a distance from the ellipse center location of the bile outflow port 34 to an outer surface thereof is regarded as the minor radius or the major radius of the ellipse.

As a material of the membrane 30, for example, fluorine resins, such as PTFE (polytetrafluoroethylene), polyester resins, such as polyethylene terephthalate, or the like can be preferably used. Membrane-shaped members prepared by such resin materials are relatively high in biocompatibility and durability and also are chemically stable. Besides, polyamide resins, such as nylon, polyurethane resins, polybutadiene resins, silicone resins or the like may be used as a material of the membrane.

Each of two support members 40, 50 is a substantially V-shaped wire material as can be seen from FIG. 1C. One support member 40 is located on the right side as viewing the biliary stent 1 from the bile outflow port 34 side and is provided outside the membrane 30. The other support member 50 is located on the left side as viewing the biliary stent 1 from the bile outflow port 34 side and is provided outside the membrane 30. Each of One ends 42 and 52 of each of the support members 40, 50 is connected to the frame 12 of the stent body 10 and each of the other ends 44, 54 (a valley part in the V-shape) is connected to the vicinity of the bile outflow port 34 (an edge of the bile outflow port 34, i.e., both end portions 36, 37 thereof shown in FIG. 3B).

As materials of the support members 40, 50, a known metal or metal alloy typified, for example, by stainless steels, such as SUS316L, Ni—Ti alloys, Cu—Zn alloys, Ni—Al alloys, titanium alloys, or the like can be preferably used.

As shown in FIG. 1D, the support members 40, 50 are arranged at locations opposed to each other and interposing the tube axis 10ax of the stent body 10, and are configured to exert forces on the bile outflow port 34 along directions away from each other (directions indicated by outlined arrows shown in FIGS. 1D and 2A).

Referring to FIG. 4 for the detailed description, the biliary stent is configured such that when a straight-line distance between the other ends 44, 54 of the support members 40, 50 to which the membrane 30 is attached is designated as M and a straight-line distance between the other ends 44, 54 of the support members 40, 50 from which the membrane 30 is detached is designated as L, a relation of M<L is satisfied, and also with respect to a peripheral length C of the bile outflow port 34 from which the support members 40, 50 are detached, a relation of 2 L≥C is satisfied. Namely, the peripheral length C of the bile outflow port 34 before the support members 40, 50 are attached thereto is equal to or smaller than two times of the straight-line distance L between the other ends 44, 54. Therefore, the other ends 44, 54 of the support members 40, 50 is bent inward by attaching the membrane 30 to the support members 40, 50. Because the other ends 44, 54 of the support members 40, 50 bent inward has a force of restoring an original state thereof acted thereon, forces are exerted on the bile outflow port 34 in directions away from each other (directions indicated by outlined arrows shown in FIGS. 1D and 2A). In addition, because such forces are exerted on the bile outflow port 34, the bile outflow port 34 when bile is not flowed therethrough (an internal pressure is not exerted thereon), is closed in a straight line shape as shown in FIG. 2A.

In other words, in a state where bile does not pass through the inside of the biliary stent 1 (a state where an internal pressure is not exerted thereon), both end portions 36, 37 of the bile outflow port 34 are pulled by forces of two support members 40, 50 attempting to be opened in directions away from each other, and as a result, the bile outflow port 34 is closed. In this case, a shape of an end face of the bile outflow port 34 is of a linear shape, such as a substantially straight line, as shown in FIG. 2A. Then, when bile flows from a gallbladder toward a duodenum to pass through the inside of the biliary stent 1, the bile outflow port 34 is opened by an internal pressure (see FIG. 2B), thereby allowing the bile to pass therethrough. A shape (opening shape) of the bile outflow port 34 when being opened is not particularly limited if passage of bile is allowed, but according to the first embodiment, is an ellipse. Preferably, this ellipse has the major radius a that is equal to or greater than two times the minor radius b (a≥2b) as shown in FIG. 2C.

Here, as an example of methods of fabricating the biliary stent 1 according to the first embodiment, a method of fabricating by dipping will be described. First, a mold is immersed in a solution prepared by dissolving a resin material of the membrane 30. The mold is, for example, a cylindrical or circular column-shaped metal member and is provided, on one end thereof, with a conical portion for shaping the bile outflow port 34. A shape of an end face of a protruding end part in the conical portion is an ellipse having the major radius a that is equal to or greater than two times the minor radius b (a≥2b), and corresponds to the shape of the end face of the bile outflow port 34 shown in FIG. 3B.

Next, in a state where the solution is attached to the mold, a solvent is evaporated and a thin film is removed from the mold, thereby obtaining a tubular body made of the resin material of the membrane 30. A part of the tubular body, which corresponds to the bile outflow port 34, is radially pulled to become a flattened shape and both ends in a longitudinal direction of the end surface thereof are heat-pressed, thereby obtaining the membrane 30.

Then, the stent body 10 and the support members 40, 50 are inserted inside the membrane 30 and are connected to each other, for example, by thermal welding. In this way, the biliary stent 1 can be obtained.

Figure 5:
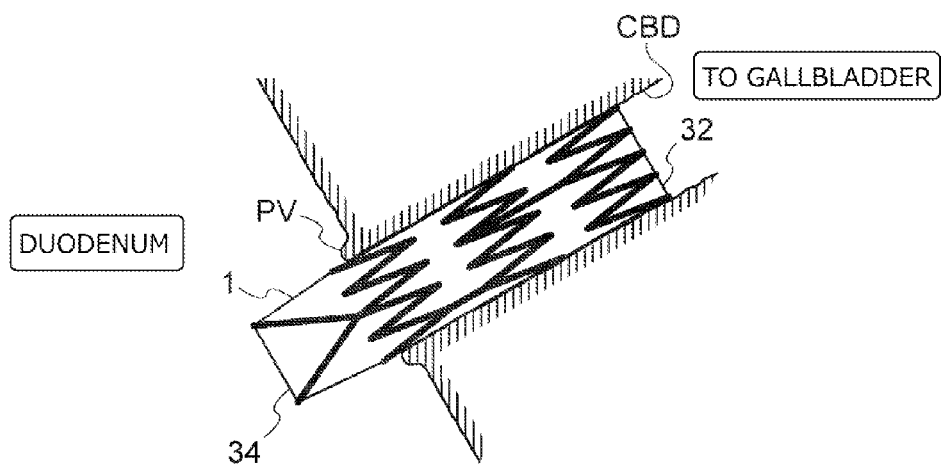
FIG. 5 is a view schematically showing a state where the biliary stent 1 is indwelled in a biliary tract.

Now, an orientation of the biliary stent 1 when the biliary stent 1 is indwelled in a biliary tract and a valve function of the biliary stent 1 will be described with reference to FIG. 5. FIG. 5 is a view schematically showing a state where the biliary stent 1 is indwelled in the biliary tract. In FIG. 5, a case is shown by way of an example, in which the biliary stent 1 is indwelled in a common bile duct CBD because an Oddi's sphincter existing around a major duodenal papilla (papilla Vater) PV does not normally function. Also, a main pancreatic duct is omitted and not shown.

When the biliary stent 1 is indwelled in the common bile duct CBD, the biliary stent 1 is indwelled so that, as shown in FIG. 5, the bile inflow port 32 is oriented toward a gallbladder and the bile outflow port 34 is oriented toward a duodenum. Although a description on a method of indwelling the biliary stent 1 in the common bile duct CBD is omitted herein, the biliary stent 1 may be indwelled in the common bile duct CBD, for example, using procedures, such as endoscopic biliary stent placement or percutaneous transhepatic biliary stent placement.

When the biliary stent 1 is indwelled in the biliary tract in the above orientation, bile flowed out from the gallbladder flows smoothly from the bile inflow port 32 through the inside of the stent body 10 and then from the bile outflow port 34 toward the duodenum. A backflow from the duodenum to the gallbladder is prevented by the bile outflow port 34 closed in a linear shape (see FIG. 2A).

According to the biliary stent 1 of the first embodiment configured as described above, because two support members 40, 50 are arranged at locations opposed to each other and interposing the tube axis 10ax of the stent body 10, and are configured to exert forces on the bile outflow port 34 along directions away from each other, the bile outflow port 34 is closed in a linear shape (a substantially straight line) when no flow is present from the gallbladder toward the duodenum. If the biliary stent 1 of the first embodiment is indwelled in the biliary tract as shown in FIG. 5, bile from the gallbladder flows through the inside of the stent body 10 and then from the bile outflow port 34 toward the duodenum, and a backflow thereof from the duodenum to the gallbladder is prevented by the bile outflow port 34 closed in a linear shape. Namely, a valve function can be exhibited by the membrane 30 and two support members 40, 50.

Also, according to the biliary stent 1 of the first embodiment, because each of the other ends 44, 54 of two support members 40, 50 is connected to the vicinity of the bile outflow port 34, the membrane 30 is not turned over toward the gallbladder even if a pressure exerted on the membrane 30 from the duodenum side is higher as compared to a pressure exerted on the membrane 30 from the gallbladder side, and thus a protruding direction of the membrane 30 can be kept. Namely, even if the entire length of the biliary stent is shortened as compared with conventional ones by reducing a length of the membrane, the valve function described above can be sufficiently exhibited.

Accordingly, the biliary stent 1 of the first embodiment has sufficient valve function while reducing the entire length of the biliary stent as compared with conventional ones.

According to the biliary stent 1 of the first embodiment, because a relationship of the straight-line distance L between the other ends 44, 54 of two support members 40, 50 from which the membrane 30 is detached and the peripheral length C of the bile outflow port 34 from which the support members 40, 50 are detached satisfies the relation of 2 L≥C described above, the configuration that 'two support members 40, 50 exert forces on the bile outflow port 34 along directions away from each other' can be achieved relatively easily.

According to the biliary stent 1 of the first embodiment, the shape of the end face of the bile outflow port 34 in the membrane 30 from which the support members 40, 50 are detached is an ellipse, and the ellipse has the major radius that is equal to or greater than two times the minor radius. When the shape of the end face is the ellipse, the shape is not so largely deviated from a shape of the bile outflow port 34 when being closed, forces required to close the bile outflow port 34 can be limited to be relatively small. As a result, a biliary stent allowing a large flexibility in selection of materials for two support materials 40, 50 and membrane 30 can be achieved relatively easily.

According to the biliary stent 1 of the first embodiment, two support members 40, 50 are provided on an outer side of the membrane 30. Therefore, because two support members do not exist inside the membrane 30, generation of an undesired gap when the bile outflow port 34 has been closed can be prevented.

According to the biliary stent 1 of the first embodiment, because the membrane 30 is configured to cover the inner peripheral surface of the stent body 10, substances to be digested or the like are hardly adhered on the inner surface of the biliary stent 1.

Variant of First Embodiment

According to the first embodiment, the shape of the end face of the bile outflow port 34 of the membrane 30 may have, for example, a shape in which a central portion in a longitudinal direction of the end surface has a narrow width as compared to both ends thereof. Specifically, as shown in FIG. 3C, two opposing sides of a bile outflow port 34*a* of a membrane 30 may be of a so-called double concave shape, in which the central portions 35*a* with respect to the longitudinal direction of the end surface are curved inward to be approached to each other and a width of the central portions 35*a* is narrower than widths of respective end portions 36*a*, 37*a*.

Like the membrane 30 of the first embodiment, the membrane 30*a* according to the variant of the first embodiment can be fabricated by forming a tubular body, for example, by dipping and then heat-pressing both ends in a longitudinal direction of an end surface in a part of the tubular body, which corresponds to the bile outflow port 34*a*.

Second Embodiment

Figure 6A:
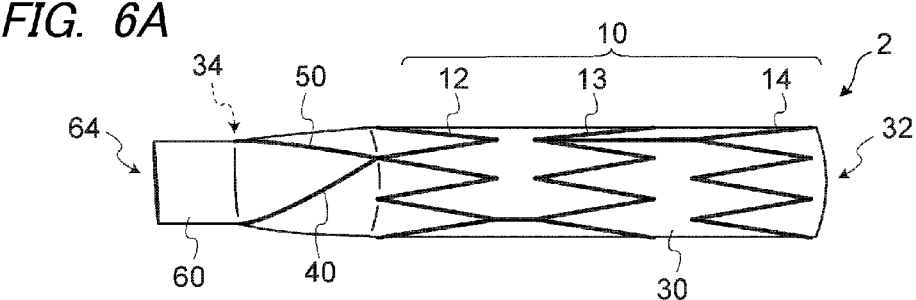
Figure 6B:
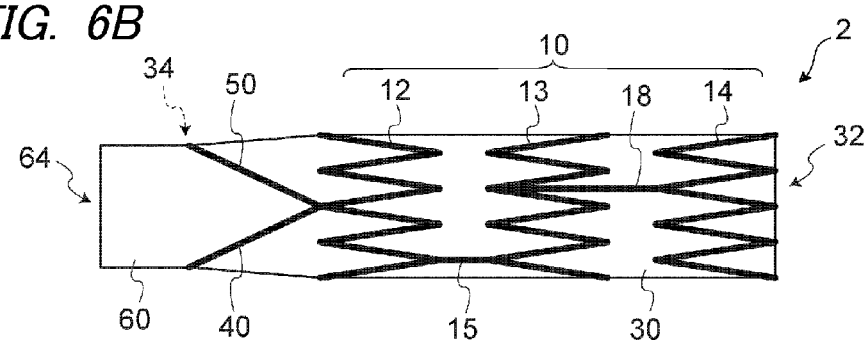
Figure 6C:
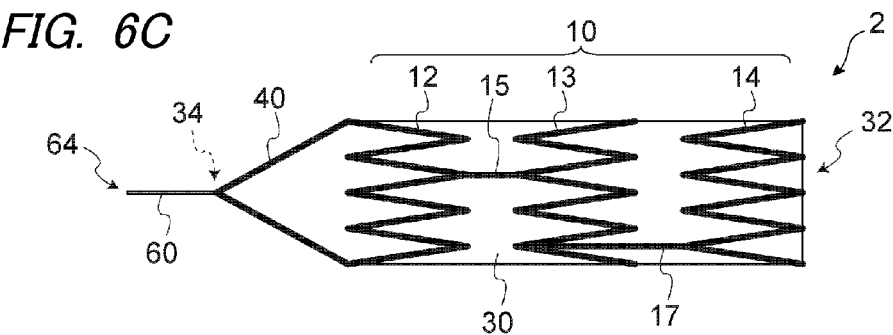
Figure 6D:
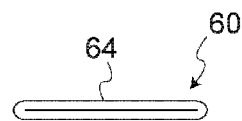
Figure 6E:

FIGS. 6A to 6E are views illustrating a biliary stent 2 according to a second embodiment. FIG. 6A is a perspective view schematically showing the biliary stent 2, FIG. 6B is a top view of the biliary stent 2, FIG. 6C is a side view of the biliary stent 2, FIG. 6D is an end view of a streamer portion 60 when a bile outflow port 34 is closed, and FIG. 6E is an end view of the streamer portion 60 when the bile outflow port 34 is opened. In FIGS. 6A to 6E, the same members as those in FIG. 1 are designated by the same reference signs and the description thereof will be omitted. Further, in FIGS. 6D and 6E, a thickness of the streamer portion 60 is shown in an exaggerated manner for easy understanding of the invention.

The biliary stent 2 of the second embodiment has basically a configuration very similar to the biliary stent 1 of the first embodiment, but is different from the biliary stent 1 of the first embodiment in that the streamer portion 60 is additionally provided as shown in FIGS. 6A to 6C.

The streamer portion 60 is a tubular member and is connected to a bile outflow port 34 of a membrane 30. According to the biliary stent 2 of the second embodiment, the streamer portion 60 is formed integrally with the membrane 30.

Like the biliary stent 1 of the first embodiment, an end portion 64 of the streamer portion 60 when bile does not pass through the inside of the biliary stent 2 (an internal pressure is not exerted thereon) is closed, and a shape thereof is of a linear shape, such as a substantially straight line, as shown in FIG. 6D. When bile flows from a gallbladder toward duodenum to pass the inside of the biliary stent 2, the end portion 64 of the streamer portion 60 is opened by an internal pressure. A shape (opening shape) of the end portion 64 of the streamer portion 60 when being opened is not particularly limited if passage of bile is allowed, but as shown in FIG. 6E, is an ellipse.

As a material of the streamer portion 60, for example, fluorine resins, such as PTFE (polytetrafluoroethylene), polyester resins, such as polyethylene terephthalate, or the like can be preferably used. Besides, polyamide resins, such as nylon, polyurethane resins, polybutadiene resins, silicone resins or the like may be used as a material of the streamer portion. According to the biliary stent 2 of the second embodiment, the material of the membrane 30 and the material of the streamer portion 60 are the same. However, the membrane and the streamer portion may be formed by different materials.

When the bile outflow port 34 is opened, the end portion 64 of the streamer portion 60 is similarly opened (see FIG. 6E). Therefore, bile flowed out from the gallbladder flows smoothly from a bile inflow port 32 through the inside of the stent body 10 and then through the bile outflow port 34 and also the streamer portion 60 toward the duodenum. If a pressure exerted on the membrane 30 from the duodenum side becomes higher as compared to a pressure exerted on the membrane 30 from the gallbladder side, the bile outflow port 34 of the membrane 30 is closed and also the end portion 64 of the streamer portion 60 is closed (see FIG. 6D). As a result, a backflow from the duodenum to the gallbladder is prevented The biliary stent 2 of the second embodiment can be fabricated by the same method as those of the biliary stent 1 of the first embodiment. In this case, the membrane 30 and the streamer portion 60 are integrally formed with each other.

In this way, the biliary stent 2 of the second embodiment is different from the biliary stent 1 of the first embodiment in that the streamer portion is additionally provided, but includes two support members 40, 50 described in the first embodiment, and therefore, for the same reason as those described in connection with the first embodiment, has sufficient valve function while reducing the entire length of the biliary stent as compared with conventional ones.

According to the biliary stent 2 of the second embodiment, because the streamer portion 60 described above is additionally provided, a backflow from the duodenum to the gallbladder can be further prevented and thus the valve function can be further enhanced.

Because the biliary stent 2 of the second embodiment has the same configuration as those of the biliary stent 1 of the first embodiment, except that the streamer portion is additionally provided, the biliary stent 2 of the second embodiment has still effects associated therewith, among the effects obtained by the biliary stent 1 of the first embodiment.

Third Embodiment

Figure 7A:
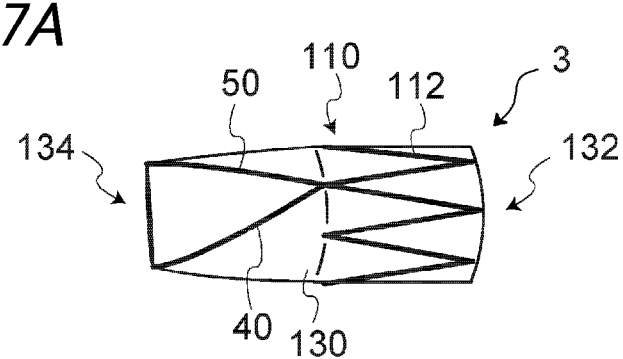
Figure 7B:
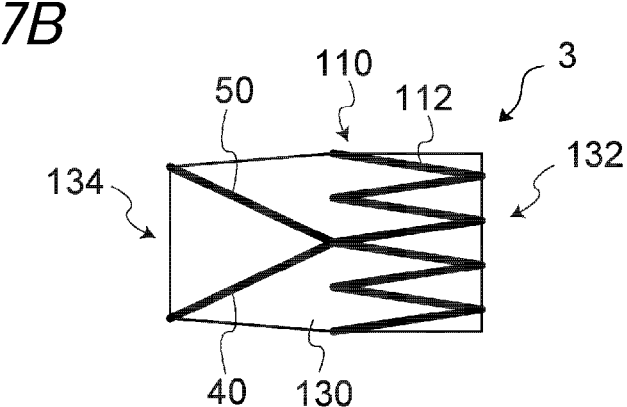

FIGS. 7A and 7B are views illustrating a biliary stent 3 according to a third embodiment. FIG. 7A is a perspective view schematically showing the biliary stent 3 and FIG. 7B is a top view of the biliary stent 3. In FIGS. 7A and 7B, the same members as those in FIG. 1 are designated by the same reference signs and the description thereof will be omitted.

Figure 8:
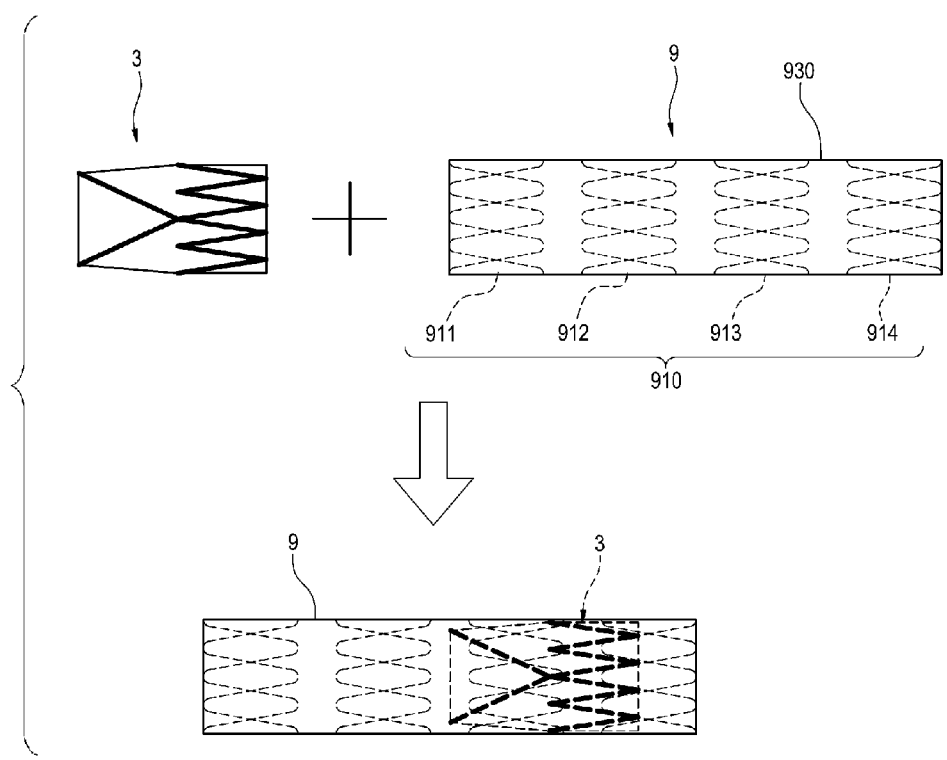
FIG. 8 is a view schematically showing an example of a method of using the biliary stent 3.

FIG. 8 is a view schematically showing an example of a method of using the biliary stent 3 according to the third embodiment.

As shown in FIG. 7A, the biliary stent 3 according to the third embodiment includes a tubular stent body 110 configured to be radially expandable, a tubular membrane 130 disposed inside the stent body 110, and two support members 40, 50 for supporting the membrane 130. The biliary stent 3 is, for example, a self-expandable biliary stent.

The stent body 110 is formed by a single frame 112 as shown in FIGS. 7A and 7B. Like the frames 12 to 14 described in the first embodiment, the frame 112 is formed by folding back a thin metal wire in a zigzag shape and is configured to have a cylindrical shape. Preferably, a known metal or metal alloy typified, for example, by stainless steels, such as SUS316L, Ni—Ti alloys, Cu—Zn alloys, Ni—Al alloys, titanium alloys, or the like can be used as materials for the metal wire forming the frame 112.

The membrane 130 is provided to protrude from one end of the stent body 110 while covering an inner peripheral surface of the stent body 110. The membrane 130 has a bile outflow port 132 and a bile outflow port 134.

The shapes of the membrane 130 (a shape of an end face of the bile outflow port 134 and an opening shape of the bile outflow port 134 when an internal pressure is exerted on the biliary stent 3) and the material of the membrane 130 are the same as those of the membrane 30 described in the first embodiment, and therefore, detailed description thereof will be omitted.

When the biliary stent 3 of the third embodiment is indwelled in a biliary tract, the biliary stent 3 can be used to be attached, as a separate body, to an inside of additional biliary stent 9, which does not have a valve function, for example, as shown in FIG. 8.

Now, a configuration of the additional biliary stent 9 will be described with reference to FIG. 8. As shown in FIG. 8, the additional biliary stent 9 is configured such that a graft member 930 formed of a resin material, such as polyester resin, is sewn onto and covers an outer side a stent body 910 having four frames 911, 912, 913, 914. The frames 911 to 914 has the same configuration as those of the frames 12 to 14 described in the first embodiment. However, the additional biliary stent 9 does not have a valve structure.

By combining the biliary stent 3 of the above third embodiment to the additional biliary stent 9, which does not have a valve structure, a valve function can be newly added thereto. In this case, a method of indwelling the biliary stent 3 is important, and if the bile inflow port 132 is oriented toward a gallbladder and the bile outflow port 134 is oriented toward a duodenum, the valve function by the membrane 130 and two support members 40, 50 can be effectively exhibited. As a result, bile from the gallbladder can be flowed toward the duodenum and also a backflow from the duodenum to the gallbladder can be prevented. In addition, after the biliary stent 3 is indwelled inside the additional biliary stent 9, even if a pressure exerted on the membrane 130 from the duodenum side is higher as compared to a pressure exerted on the membrane 130 from the gallbladder side, the membrane 130 is not turned over toward the gallbladder because the biliary stent 3 has the support members 40, 50, and thus a protruding direction of the membrane 130 can be kept. As a result, the valve function described above can be sufficiently exhibited.

In the foregoing, although the biliary stent of the present invention has been described on the basis of each of the above embodiments, the invention is not limited to each of the above embodiments, and accordingly can be embodied as various aspects without departing from the spirit and scope of the invention and, for example, modifications thereof can be made as in the following.

(1) While each of the above embodiments has been described as illustrative examples in which the shape of the end face of the bile outflow port of the membrane from which the two support members are detached is an ellipse designed to have the major radius that is equal to or greater than two times the minor radius, the present invention is not limited thereto. For example, the shape of the end face may have a double concave shape in which two opposing sides of the bile outflow port of the membrane are curved inward so that central portions in a longitudinal direction of the end surface are approached to each other as described as the variant of the first embodiment (see FIG. 3C), a plano-concave shape (piano-concave lens shape) in which only one side of two opposing sides of the bile outflow port of the membrane is curved inward, or a concave meniscus shape (concave meniscus lens shape) in which one side of two opposing sides of the bile outflow port of the membrane is curved inward and the other side is curved outward. Alternatively, it may be a flattened shape such as a rectangular shape.

(2) While each of the above embodiments has been described as illustrative examples in which two support members are provided on an outer side of the membrane, the present invention is not limited thereto, and two support members may be provided inside the membrane or may be embedded in the membrane. In the case where two support members are provided on an inner side of the membrane or embedded in the membrane, if the shape of the end face of the bile outflow port is of an ellipse set to be 'major radius a≧minor radius 2b', the minor radius or major radius of the ellipse means a distance from the ellipse center location to an inner surface of the bile outflow port.

(3) While each of the above embodiments has been described as illustrative examples in which the membrane is disposed on an inner side of the stent body, the present invention is not limited thereto, and the membrane may be disposed on an outer side of the stent body, or the stent body may be embodied in the membrane. In the case where the membrane is covered outside the stent body or the stent body is embedded in the membrane, there is a merit that when the biliary stent of the present invention is necessary to be withdrawn after the biliary stent is indwelled in a biliary tract, the biliary stent can be easily withdrawn.

(4) While the first and second embodiments have been described as illustrative examples in which the stent body 10 has three frames 12 to 14 connected to each other by connection members 15 to 18, the present invention is not limited thereto, and a stent body formed by any other configurations, such as those having four or more frames or those having a continuous frame without connection members, may be employed. Similarly, the third embodiment is not limited to the stent body 110 having one frame 112, and accordingly, a stent body having two or more frames may be employed.

(5) While each of the above embodiments has been described as illustrative examples in which the stent body and the support members are made of metal materials, the present invention is not limited thereof, and accordingly, for example, ceramics, resins or the like may be employed as materials thereof.

(6) While each of the above embodiments has been described as illustrative examples in which the stent body and the support members are connected with the membrane by thermal welding, the present invention is not limited thereto. For example, any other bonding method, such as stitching using a stitching thread, adhesives, or solvents, may be employed for such connection.

(7) While the second embodiment has been described as an illustrative example in which the membrane 30 and the streamer portion 60 are integrally formed with each other, the present invention is not limited thereto, and the membrane and the streamer portion may be bonded to each other by any means, such as adhesion, after the membrane and the streamer portion are respectively formed as separate bodies.

(8) While the third embodiment has been described as an illustrative example in which the additional biliary stent 9 is formed such that the graft member 930 is sewn onto and covers the outer side of the stent body 910 and the biliary stent 3 is indwelled inside of the additional biliary stent 9 having no valve structure, the additional biliary stent is not limited thereto, and the biliary stent 3 may be indwelled, for example, in a biliary stent having a graft member sewn onto and covering an inner side of a stent body, or in a biliary stent formed only from a metallic stent body, so-called as a metallic stent.

(9) While each of the above embodiments has been described as illustrative examples in which the biliary stent is a self-expandable type, the present invention is not limited thereto, and the invention may be applied to a balloon-expandable biliary stent.

(10) With regard to a location where the biliary stent according to the present invention is indwelled, while the first embodiment has been described as an illustrative example in which the biliary stent is indwelled in a major duodenal papilla part, which corresponds to a duodenum-side outlet of the common bile duct as shown in FIG. 5, the invention is not limited thereto. For example, the biliary stent according to the present invention can be undoubtedly indwelled in locations on the common bile duct, which are located more toward the gallbladder, such as a location near a part at which a cystic duct and a common hepatic duct are joined with each other.

(11) While each of the above embodiments has been described as illustrative examples in which both ends in a longitudinal direction of an end surface on a part, which corresponds to the bile outflow port, are heat-pressed upon fabrication of the membrane, the present invention is not limited thereto. For example, the part may be pressed using ultrasonic waves or high frequency waves, or the part may be bonded (welded) using an adhesive or a solvent.

(12) While each of the above embodiments has been described as illustrative examples in which a shape (opening shape) of the bile outflow port when being opened is an ellipse, the shape is not particularly limited if bile can be outflowed.

EXAMPLES

While the present invention will hereinafter be described in more detail with reference to examples and comparative examples, the invention is not limited in any way by the following examples, as long as it does not extend beyond the scope of the invention.

Example

Based on the configuration of the biliary stent 1 according to the first embodiment described above, the Example was provided to have two support members supporting a membrane from the outer surface of the membrane that is arranged inside a stent body and is provided to protrude from one end of the stent body. Specifically, samples according to the Example were prepared such that a tubular membrane made of a soft polyvinyl chloride resin (75 parts (phr) of DEHP added) is welded by an organic solvent inside a stent body and two support members made of Ni—Ti alloy. The stent body had a stent diameter of 10 mm upon expansion and a part of the membrane welded with the stent body had a diameter of 10 mm. An opening shape of a bile outflow port was an ellipse and a peripheral length C of the bile outflow port was approximately 18 mm. Also, a straight-line distance L between the other ends of two support members before the membrane was attached thereto was approximately 12 mm. Namely, the samples according to Example satisfied a relation of 2 L>C and were configured such that two support members exerted forces on the bile outflow port along directions away from each other.

Comparative Example

The Comparative Example was provided by simply arranging a tubular membrane inside a stent body (i.e., does not have two support members). Specifically, samples according to Comparative Example were prepared such that a tubular membrane made of a soft polyvinyl chloride resin (75 parts (phr) of DEHP added) is welded inside a stent body made of Ni—Ti alloy by an organic solvent. The stent body had a stent diameter of 10 mm upon expansion. The membrane formed by a straight tube having a diameter of 10 mm was arranged inside the stent body. Namely, an opening shape of a bile outflow port was a perfect circle.

With respect to the samples according to Example and Comparative Example described above, the following two tests were performed to evaluate a valve function of each sample.

Test 1

Test 1 is for evaluating patency of biliary stents with respect to a flow directed from a gallbladder to a duodenum. Upon evaluating of the patency of biliary stents, samples according to Example and Comparative Example were indwelled in a mock biliary tract shown in FIGS. 9A and 9B and then a communication state of a liquid flowing in the mock biliary tract was checked, thereby performing sensory evaluation about the patency of biliary stents.

Figure 9A:
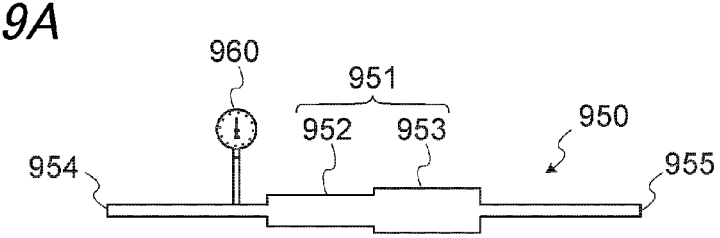
Figure 9B:
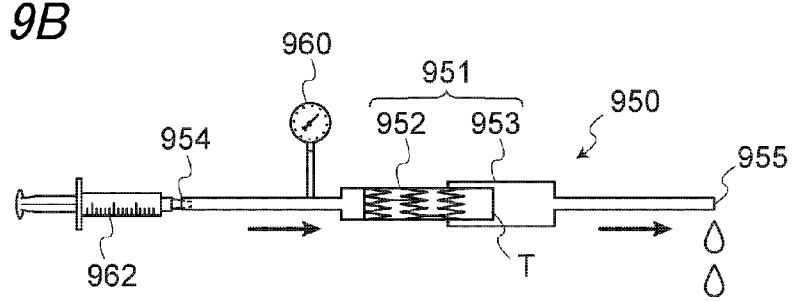

FIGS. 9A and 9B are views illustrating the mock biliary tract 950 used in Test 1. FIG. 9A is a view showing the mock biliary tract 950 before each of samples is disposed therein and FIG. 9B is a view schematically showing a state where a liquid is communicated through a sample T indwelled in the mock biliary tract 950.

(1) Test Method—First, the mock biliary tract 950 shown in FIG. 9A was prepared. The mock biliary tract 950 was a tubular member made of polyvinyl chloride resin. The mock biliary tract 950 had an indwelling portion 951 for indwelling a sample, an injection port 954 to be connected to a syringe 962, and an outlet port 955 for discharging a liquid in the mock biliary tract 950. The indwelling portion 951 was a small diameter part 952 and a large diameter part 953 and was formed in a stepped shape. The small diameter part 952 had a tube diameter of 9 mm. To the mock biliary tract 950 having such a configuration, a manometer 960 (produced by Nidec Copal Electronics Corporation) was provided.

Samples according to Example and Comparative Example were indwelled in the indwelling portion 951 of the prepared mock biliary tract 950. Samples ware indwelled so that a portion thereof protruded from the small diameter portion 952 to the large diameter portion 953, assuming a so-called transpapillary placement. Then, in a state where the mock biliary tract 950 was filled with a salad oil, the syringe 962 filled with a colored water was connected to the injection port 954, and the colored water in the syringe 962 was injected into the mock biliary tract 950. Upon injection of the colored water, a pressure indicated by the manometer 960 was less than 2 mmHg. The colored water that can be clearly separated from the salad oil filled in the mock biliary tract 950 was used to fill in the syringe 962, and therefore, a flow of the colored water injected from the syringe 962 was visually observed sufficiently.

(2) Evaluation Method—After the colored water was injected into the mock biliary tract 950, a communication state (a degree of outflow of the colored water flowed out samples) of the colored water for samples was scored by visually checking. The scores (hereinafter, patency scores) were classified as 'score 0' in a case where the colored water, which was flowed into samples from the small diameter portion 952 side, was not flowed out toward the large diameter portion 953 at all, as 'score 1' in a case where a small amount of the colored water was flowed out toward the large diameter portion 953, as 'score 2' in a case where the colored water was flowed out toward the large diameter portion 953 but a small resistance was observed (the degree of outflow was large as compared to when being score 1), and as 'score 3' in a case where the colored water was flowed out toward the large diameter portion 953 without any problems (resistance was hardly observed).

(3) Test Results—In all samples according to Example and Comparative Example, the patency scores were 'score 3'. Namely, the patency of samples according to Example was the same degree as those of samples according to Comparative Example. From this, it was found that the biliary stents according to Example have a sufficient patency with respect to a flow directed from the gallbladder to the duodenum.

Test 2

Test 2 is for evaluating backflow prevention ability of biliary stents with respect to a flow directed from a duodenum to a gallbladder. Upon evaluating of the backflow prevention ability of biliary stents, samples according to Example and Comparative Example were indwelled in a mock biliary tract shown in FIGS. 10A and 10B and then a communication state of a liquid flowing in the mock biliary tract was checked, thereby performing sensory evaluation about the backflow prevention ability of biliary stents.

Figure 10A:
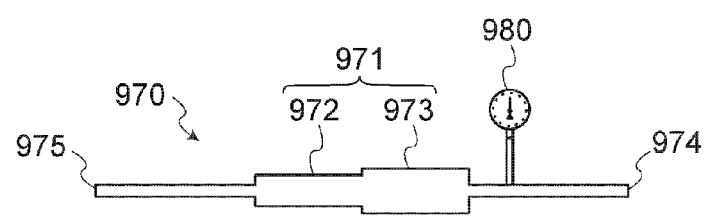
Figure 10B:
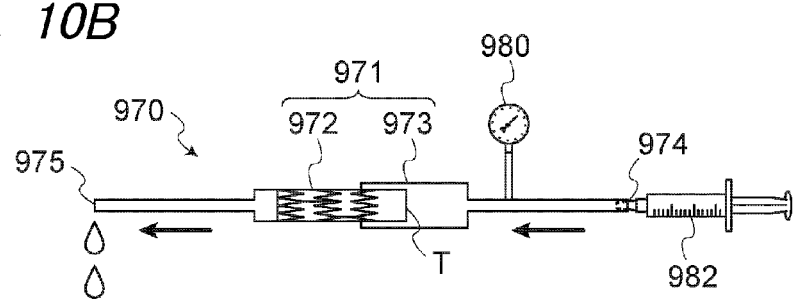

FIGS. 10A and 10B are views illustrating the mock biliary tract 970 used in Test 2. FIG. 10A is a view showing the mock biliary tract 970 before each of samples is disposed therein and FIG. 10B is a view schematically showing a state where a fluid is not communicated through a sample T indwelled in the mock biliary tract 970.

(1) Test Method—First, the mock biliary tract 970 shown in FIG. 10A was prepared. The mock biliary tract 970 was a tubular member made of polyvinyl chloride resin. The mock biliary tract 970 had an indwelling portion 971 for indwelling a sample, an injection port 974 to be connected to a syringe 982, and an outlet port 975 for discharging a liquid in the mock biliary tract 970. The indwelling portion 971 was a small diameter part 972 and a large diameter part 973 and was formed in a stepped shape. The small diameter part 972 had a tube diameter of 9 mm. To the mock biliary tract 970 having such a configuration, a manometer 980 was provided.

Samples according to Example and Comparative Example were indwelled in the indwelling portion 971 of the prepared mock biliary tract 970. Samples ware indwelled so that a portion thereof protruded from the small diameter portion 972 to the large diameter portion 973, assuming a so-called transpapillary placement. Then, in a state where the mock biliary tract 970 was filled with a salad oil, the syringe 982 filled with a colored water was connected to the injection port 974, and the colored water was injected into the mock biliary tract 970 while exerting a pressure by the syringe 982 until a value of the manometer 980 became 20 mmHg.

(2) Evaluation Method—After the colored water was injected into the mock biliary tract 970, a communication state (a degree of outflow of the colored water flowed out samples) of the colored water for samples was scored by visually checking. The scores (hereinafter, backflow prevention scores) were classified as 'score 0' in a case where the colored water was flowed out toward the small diameter portion 972 without a resistance, as 'score 1' in a case where the colored water was flowed out toward the small diameter portion 972 but a small resistance was observed, as 'score 2' in a case where a small amount of the colored water was flowed out toward the small diameter portion 972 (the degree of outflow was small as compared to when being score 1), and as 'score 3' in a case where the colored water, which was flowed into samples from the large diameter 973 side was flowed out toward the small diameter portion 972.

(3) Test Results—The backflow prevention scores in samples according to Comparative Example were 'score 0', whereas the backflow prevention scores in samples according to Example were 'score 3'. Namely, the backflow prevention ability of samples according to Example was much higher than those of samples according to Comparative Example. From this, it was found that the biliary stents according to Example have a sufficient backflow prevention ability with respect to a flow directed from the duodenum to the gallbladder.

[Summary of Test 1 and 2] From Test 1, it was found that the biliary stents according to Example have a sufficient patency with respect to a flow directed from the gallbladder to the duodenum. From Test 2, it could be also found that the biliary stents according to Example have a sufficient backflow prevention ability with respect to a flow directed from the duodenum to the gallbladder. From the foregoing, it can be found that the biliary stent according to Example (i.e., the biliary stent of the present invention) has a sufficient good valve function.

While the present invention has been described in detail with reference to specific embodiments thereof, those skilled in the art will appreciate that various changes and modifications may be made therein without departing from the sprit and scope of the present invention. This application is based on Japanese Patent Application No. 2012-016681 filed on Jan. 30, 2012, the entire content of which is incorporated herein by reference.

EXPLANATION OF REFERENCE SIGNS 1, 2, 3 Biliary Stent
9 Additional Biliary Stent
10, 110, 910 Stent Body
10ax Tube Axis of Stent Body
12-14, 112, 911-914 Frame
15-18 Connection Member
30, 30a, 130 Membrane
32, 132 Bile Inflow Port
34, 34a, 134 Bile Outflow Port
35, 35a Central Portion (with respect to longitudinal direction of end surface of bile outflow port)
36, 36a, 37, 37a End Portion (with respect to longitudinal direction of end surface of bile outflow port)
40, 50 Support Member 42, 52 One End of Support member
44, 54 Other End of Support Member
60 Streamer Portion
64 End Portion of Streamer Portion
930 Graft Member
950, 970 Mock Biliary Tract
951, 971 Indwelling Portion
952, 972 Small Diameter Portion
953, 973 Large Diameter Portion
954, 974 Injection Port
955, 975 Outlet Port
960, 980 Manometer
962, 982 Syringe
CBD Common Bile Duct
PV Major Duodenal Papilla (papilla Vater)
T Sample

The invention claimed is:

1. A biliary stent comprising:
a tubular stent body configured to be radially expandable;
a tubular membrane provided to protrude from one end of the stent body and having a bile outflow port; and
two support members supporting the membrane;
wherein one end of each of the two support members is connected to the one end of the stent body,
another end of each of the two support members is connected to a vicinity of the bile outflow port,
the two support members are arranged at locations opposed to each other and interposing a tube axis of the stent body, and are configured to exert forces on the bile outflow port along directions away from each other, and
a shape of an end face of the bile outflow port of the membrane from which the two support members are detached is flattened.

2. The biliary stent according to claim 1, wherein the biliary stent is configured to satisfy a relation of 2 L≥C,
wherein L is a straight-line distance between the other ends of the two support members from which the membrane is detached; and
C is a peripheral length of the bile outflow port of the membrane from which the two support members are detached.

3. The biliary stent according to claim 1, wherein the shape of the end face of the bile outflow port is an ellipse, and
the major radius of the ellipse is equal to or greater than two times the minor radius.

4. The biliary stent according to claim 1, wherein the shape of the end face of the bile outflow port is configured such that a central portion with respect to a longitudinal direction of the end face is narrower than respective end portions.

5. The biliary stent according to claim 1, wherein the two support members are provided on an outer side of the membrane.

6. The biliary stent according to claim 1, wherein the two support members are provided on an inner side of the membrane.

7. The biliary stent according to claim 1, wherein the two support members are embedded in the membrane.

8. A biliary stent comprising:
a tubular stent body configured to be radially expandable;
a tubular membrane provided to protrude from one end of the stent body and having a bile outflow port;
two support members supporting the membrane; and
a tubular streamer portion connected to the bile outflow port,
wherein one end of each of the two support members is connected to the one end of the stent body,
another end of each of the two support members is connected to a vicinity of the bile outflow port, and
the two support members are arranged at locations opposed to each other and interposing a tube axis of the stent body, and are configured to exert forces on the bile outflow port along directions away from each other.

9. The biliary stent according to claim 8, wherein the biliary stent is configured to satisfy a relation of 2 L≥C,
wherein L is a straight-line distance between the other ends of the two support members from which the membrane is detached; and
C is a peripheral length of the bile outflow port of the membrane from which the two support members are detached.

10. The biliary stent according to claim 8, wherein a shape of an end face of the bile outflow port of the membrane from which the two support members are detached is flattened.

11. The biliary stent according to claim 10, wherein the shape of the end face of the bile outflow port is an ellipse, and
the major radius of the ellipse is equal to or greater than two times the minor radius.

12. The biliary stent according to claim 10, wherein the shape of the end face of the bile outflow port is configured such that a central portion with respect to a longitudinal direction of the end face is narrower than respective end portions.

13. The biliary stent according to claim 8, wherein the two support members are provided on an outer side of the membrane.

14. The biliary stent according to claim 8, wherein the two support members are provided on an inner side of the membrane.

15. The biliary stent according to claim 8, wherein the two support members are embedded in the membrane.

* * * * *